US006418338B1

(12) United States Patent
Barbera-Guillem et al.

(10) Patent No.: US 6,418,338 B1
(45) Date of Patent: Jul. 9, 2002

(54) METHOD FOR DETECTING AND SURGICALLY REMOVING LYMPHOID TISSUE INVOLVED IN TUMOR PROGRESSION

(75) Inventors: Emilio Barbera-Guillem, Powell; Edward W. Martin, Jr., Delaware, both of OH (US)

(73) Assignee: Phylatron Ltd., Westerville, OH (US)

( * ) Notice: Subject to any disclaimer, the term of this patent is extended or adjusted under 35 U.S.C. 154(b) by 0 days.

(21) Appl. No.: 09/244,369

(22) Filed: Feb. 4, 1999

Related U.S. Application Data

(60) Provisional application No. 60/077,970, filed on Mar. 13, 1998, and provisional application No. 60/073,882, filed on Feb. 6, 1998.

(51) Int. Cl.[7] .................................................. A61B 5/00
(52) U.S. Cl. ....................................................... 600/436
(58) Field of Search ........................... 128/898; 600/436

(56) References Cited

U.S. PATENT DOCUMENTS 4,782,840 A 11/1988 Martin, Jr. et al.
5,464,013 A * 11/1995 Lenelson .................... 600/436
5,590,656 A * 1/1997 O'Nonisio et al. ......... 600/436
5,716,595 A 2/1998 Goldenberg

OTHER PUBLICATIONS

Babino et al., Molecular Cloning of a Monoclonal Anti–Tumor Antibody Specific for the Tn Antigen and Expression of an Active Single–Chain Fv Fragment; HYBRIDOMA vol. 16, No. 4, Aug. 1997, pp. 317–324.

Barbera–Guillem et al., First Results for Resetting the Antitumor Immune Response by Immune Corrective Surgery in Colon Cancer; Am. J. Surg. vol. 176, Oct. 1998, pp. 339–343.

* cited by examiner

*Primary Examiner*—William E. Kamm
(74) *Attorney, Agent, or Firm*—M. Bud Nelson

(57) ABSTRACT

A method is provided for immune corrective surgical removal of lymphoid tissues containing shed tumor antigen in an individual. A detector molecule, with binding specificity for shed tumor antigen, is administered to an individual, and detected in the individual is the presence of lymphoid tissue which contains shed tumor antigen, as detected by the signal emitted by the detector molecule bound to shed tumor antigen. The lymphoid tissue, detected as containing shed tumor antigen, may then be surgically removed, thereby removing B cells, shed tumor antigen, and follicular dendritic cells involved in a pro-tumor immune response that are contained in the removed lymphoid tissue.

8 Claims, 6 Drawing Sheets

α-sTAA-Ab

-α-sTAA-Ab
α-sTAA-Ab
sTAA
FDC
LT
γ-DETECTOR
Surgical Removal

METHOD FOR DETECTING AND SURGICALLY REMOVING LYMPHOID TISSUE INVOLVED IN TUMOR PROGRESSION

This is a nonprovisional application based on earlier abandoned provisional applications Ser. No. 60/073,882 filed Feb. 6, 1998 and Ser. No. 60/077,970 filed Mar. 13, 1998 which are herein incorporated by reference.

FIELD OF THE INVENTION

The present invention is related to novel methods and for surgical therapy associated with solid, non-lymphoid tumor types. More particularly, the present invention is related to the methods for detecting, and surgically removing lymphoid tissues which contain deposits of shed tumor antigen and B lymphocytes involved in promotion of tumor cell invasion and metastasis.

BACKGROUND OF THE INVENTION

1. Immunopathology

The response of an individual to tumor cells involves the reactions and counteractions mediated by both cellular and humoral arms of the immune system. Tumor cell growth may represent a disturbance in the equilibrium of the immune system that is pre-existing, and/or induced by the tumor cells themselves. However, most investigations to date have focused on the role of T cells in tumor immunity. The role of B cells in a tumor-bearing individual still remains unclear.

Previous studies have shown that lymph nodes regional to a primary tumor in cancer patients, and in in vivo experimental animal models of tumor development, can undergo a prominent expansion in the germinal centers of immune cells that include B lymphocytes (B cells)(Eremin et al., 1980, *Br. J. Cancer* 41:62; Bertschmann et al., 1984, *Br. J. Cancer* 49:477–484). However, the reason(s) for this observed B cell proliferative response remains unclear, and may be due to either activation and stimulation directly by tumor cells or tumor cell components, and/or indirectly by stimulation of T-helper cells which then activate and stimulate B cells. A recent study confirmed the increase in the number of B cells in lymph nodes regional to primary tumors (Ito et al., 1996, *Immunobiol.* 195:1–15). The number of B cells increase in the regional lymph nodes concomitantly with tumor development, and such B cells appear to be able to elicit anti-tumor immunity. In that regard, there are numerous reports that cancer patients have circulating antitumor antibodies (see, e.g., Carey et al., 1976, *Proc. Natl. Acad. Sci. USA* 73:3278–3282; Abe et al., 1989, *Cancer Res.* 80:271–276; Christensen et al., 1989, *Int. J. Cancer* 37:683–688). Thus, there appears that a humoral immune response towards tumor-associated antigens can be mounted in cancer patients. However, the role of the B cells in the host response to tumor, and the tumor associated antigens recognized by B cells, remain poorly defined.

2. Current Diagnostic and Therapeutic Implications

Several techniques, such as radioimmunodiagnosis and radioimmunoguided surgery, have been developed for the purpose of detecting tumors occult to other imaging techniques. In radioimmunodiagnosis, a patient is injected intravenously with a radiolabeled antitumor monoclonal antibody or radiolabeled antibody fragment with binding specificity for the tumor. Hours to days post-injection, the patient is then examined by immunoscintigraphy for body imaging of primary tumor and metastases. Radioimmunodiagnosis continues to be evaluated for preoperative evaluation of patients (Ryan, 1993, *Cancer* 71:4217–24). In radioimmunoguided surgery, a patient is injected with a radiolabeled anti-tumor monoclonal antibody, and exploratory surgery is carried out approximately 3–4 weeks post-injection. The 3 to 4 week period allows for the patient to clear radioactivity that is unbound to tumor cells ("background signal"). The surgeon uses a hand-held radiation detector to detect localized high counts of radioactivity representing tumor foci. These radioactive areas subsequently found visually or histologically to contain tumor cells are then resected or excised. U.S. Pat. No. 4,782,840 describes the radioimmunoguided surgery protocol in more detail. Another radioimmunoguided surgery protocol using antibody fragments for close range tumor detection, in detecting and defining tumor and tumor margins, is described in more detail in U.S. Pat. No. 5,716,595.

Using either radioimmunodiagnosis (RAIDS) or radioimmunoguided surgery (RIGS) to search for metastases from colorectal or ovarian cancer, false positivity of draining lymph nodes has been observed (for a review, see Cornelius and West, 1996, *J. Surg. Oncol.* 63:23–35; Stephens et al., 1993, *J. Nucl. Med.* 34:804–08; and Sivolapenko et al., 1995, *Lancet* 346:1662–1666). At the time of the invention, it was believed that such false positive tests result in surgical dissections that will not benefit the patient, but instead, will increase morbidity. Therefore, false positive tests "should be diligently avoided in the surgical patient"(Stephens et al., 1993, supra). For example, since false positive lymph nodes are not easily examined by palpation, such false positives are currently viewed as presenting a serious problem to general applicability of radioimmunodiagnosis and radioimmunoguided surgery (Stephens et al., 1993, supra).

False positive ("false tumor-positive") lymph nodes (LN) have been characterized as germinal center staining for noncellular tumor antigen; and classified as type III: RIGS positive, histology (hematoxylin and eosin) negative for tumor. It is estimated that of the lymph nodes detected by RAIDS or RIGS, 80% are false positive (i.e., lack evident tumor cells but contain noncellular tumor antigen). Several mechanisms to explain such false positives have been proposed. One suggested mechanism is that shed tumor antigen causes an inflammatory process mediated by the tumor antigen/ antibody complex that may also involve a T cell-mediated cytotoxic response (Stephens et al., 1993, supra). Alternately, tumor antigen is retained in the form of antigen/antibody complexes, attached to follicular dendritic cells located in the germinal centers (Cornelius and West, 1996, supra). In another proposed scenario, tumor antigen detected is primarily in sinusoidal macrophage as part of antigen processing (Cornelius and West, 1996, supra). The phenomenon of false positives is problematic, and needs to be further investigated to identify its origin and to explain its relationship, if any, to treatment options, and resultant clinical outcomes following treatment, for the affected patient.

3. Need for New Therapeutic Approaches

While new therapeutics are being developed and tested for efficacy, many of the currently available cancer treatments are relatively ineffective. It has been reported that chemotherapy results in a durable response in only 4% of treated patients, and substantially prolongs the life of only an additional 3% of patients with advanced cancer (Smith et al., 1993, *J. Natl. Cancer Inst.* 85:1460–1474). Current treatments for metastases are both cost-prohibitive, relatively ineffective, and present with major toxicity. Regarding the latter and depending on the drug or drug combination used, systemic chemotherapy may result in one or more toxicities including hematologic, vascular, neural, gastrointestinal, renal, pulmonary, otologic, and lethal.

Surgery, when possible, is used as a standard therapy for patients with isolated metastases (e.g., hepatic and/or pulmonary). After resection, the projected five year survival rate may range from 25–35%, the mean survival is about 31 months, and the 30-day mortality rate is about 4% (Wade, 1996, *J. Am. Coll. Surg.* 182:353–361). However, about 25% to 45% of patients who have had resection of their colorectal cancer later develop recurrences (Zaveidsky et al., 1994, supra). Thus, there continues to be a need for identifying processes which enhance tumor growth and metastasis. More particularly, there remains a need for a method of detecting and treating processes that contribute to tumor development at an early stage (e.g., Stage I or II) or late stage (e.g., Stage III or IV) before, during, or after surgical resection of tumor. Likewise, there remains a need for a method of detecting and treating precancerous conditions (e.g., prior to, or at an early stage of, development of primary tumor or regrowth).

SUMMARY OF THE INVENTION

Accordingly, it is a primary object of the present invention to provide a method for inhibiting the growth of primary solid, nonlymphoid tumors and their metastases.

It is another object of the present invention to provide methods for antitumor, immune corrective surgery directed to a tumor bearing individual's immune cells, wherein the immune cells promote tumor progression of the primary nonlymphoid tumor and its metastases ("pro-tumor immune response).

It is a further object of the present invention to provide a method for antitumor therapy which can be used before, during, or after surgical removal of tumor, and which is directed to one or more of deposits of shed tumor antigen, subpopulation of memory B cells activated by shed tumor antigen, plasma cells secreting antibody against shed tumor antigen, or follicular dendritic cells presenting immune complexes containing shed tumor antigen, and which are present in lymphoid tissue involved in a pro-tumor immune response in an individual.

It is also a further object of the present invention to provide a prognostic indicator of metastasis; wherein the detection of a presence of a pro-tumor immune response is a prognostic indicator that invasion and metastasis has occurred, or is likely to occur, from the local primary tumor.

It is also a further object of the present invention to provide a diagnostic and prognostic indicator of the immune process mediated (at least in part) by B cells which promote tumor development and progression of the primary tumor, wherein the detection of a deposit of shed tumor antigen in lymphoid tissues is an indicator of the immune process which can promote primary tumor progression.

The foregoing objects are achieved by identifying a novel mechanism in which certain soluble tumor antigens, shed from tumor cells of solid, nonlymphoid tumors, are capable of inducing an immune response which promotes tumor growth and metastasis, as will be more apparent from the following description. This mechanism of tumor promotion involves the specific type of immune response induced by shed tumor antigen. This specific immune response, a "pro-tumor immune response", can involve (a) the contact or presence of shed tumor antigen in relation to the cell surface of B cells, and cell surface of follicular dendritic cells or other antigen presenting cells (e.g., contained in lymphoid tissues); (b) activation of such B cells to proliferate, (c) and differentiation of the activated B cells into plasma cells which secrete anti-shed tumor antigen antibody that forms complexes with shed tumor antigen in sufficient amounts which may act indirectly (via immune effector cells) and/or directly (on the tumor cells) to mediate tumor progression. Continuous presentation of immune complexes containing shed tumor antigen by FDC plays an important role in the persistence of a pro-tumor immune response.

In one embodiment of the immune corrective surgical method of the present invention, shed tumor antigen is identified in lymphoid tissues in an individual. The lymphoid tissue containing shed tumor antigen is then surgically excised from the individual, thereby removing the activated B cells, shed tumor antigen, and shed tumor antigen presenting-follicular dendritic cells in a process for immunomodulating the immune system to prevent the tumor promoting function of these components involved in the pro-tumor immune response.

DETAILED DESCRIPTION OF THE PREFERRED EMBODIMENTS

Definitions

Figure 1:
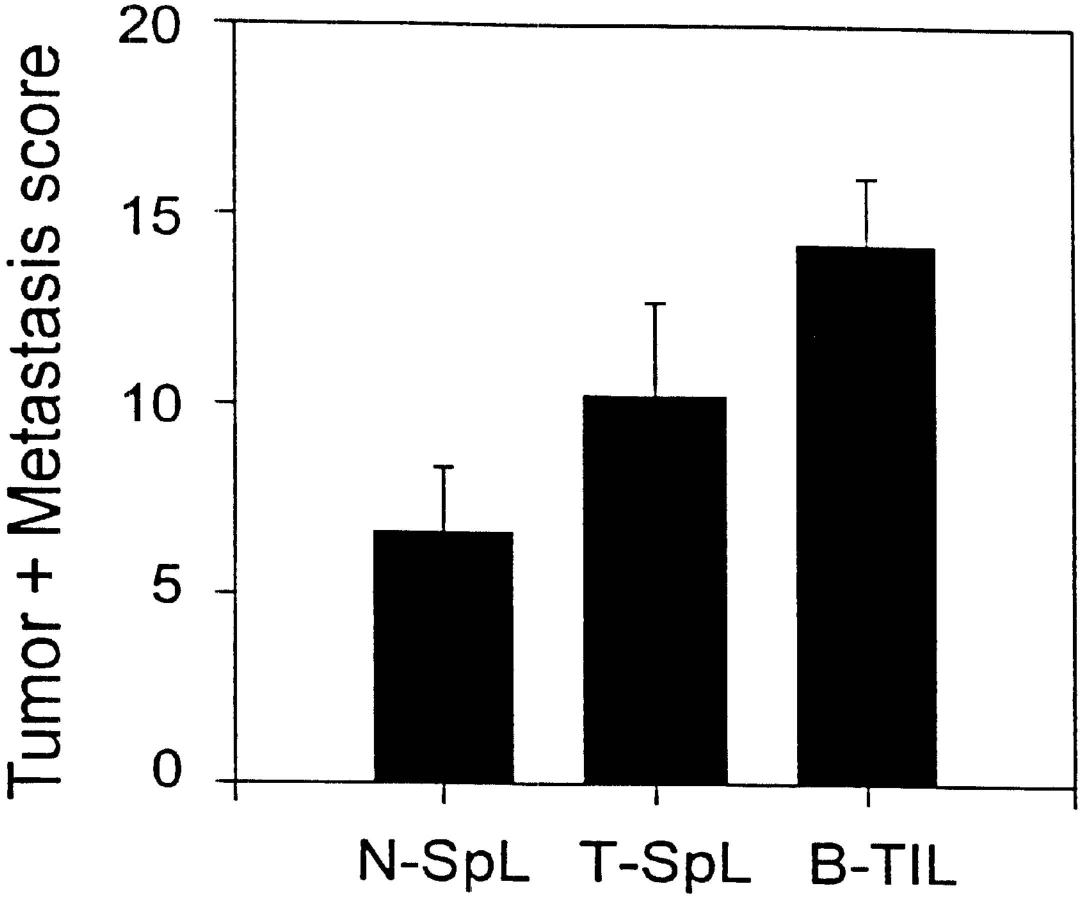
FIG. 1 is a bar graph illustrating in vivo spleen tumor cell growth and liver metastasis (combined score) in the presence of lymphoid tissue B lymphocytes from tumor bearing mice (T-SpL), B lymphocytes from tumor (B-TIL), and splenic B lymphocytes from normal mice (N-Spl).

The term "lymphoid tissue" is used herein, for purposes of the specification and claims, to mean a tissue which contains localized areas of antigen presenting cells (e.g., follicular or germinal center dendritic cells) and B cells; and which contains infiltrates ("deposits") of shed tumor antigen as detected by an administered detector molecule. An example of such localized areas comprises germinal centers. Such lymphoid tissues comprise lymphatic tissues that may include, but are not limited to, lymph nodes; milky patches in the mesenterium of the intestine; omentum; appendix; Peyer's patches; loose connective tissue (e.g., associated with vessels in the walls of the aorta); lymphatic vessels; submucosal spaces; subserosa spaces; peritoneal cavity; ligaments (e.g., gastrohepatic ligament); and epineura. For the purposes of the specification and claims, and only when specifically referring to resection by the immune corrective surgical methods according to the present invention, the spleen is excluded from such resected lymphoid tissues.

The term "B cells" is used herein, for purposes of the specification and claims, to mean mammalian (and preferably human) nonmalignant B cells. As known to those skilled in the art, malignant B cells refers to cancer cells of B cell origin, such as B cell lymphomas, and B cell leukemias. Thus, the term "B cells", as used herein in reference to an immune corrective surgical procedure according to the present invention, and in treating a pro-tumor immune response, specifically excludes B cell lymphomas, B cell leukemias, and cancer cells of B cell origin. In that regard, nonmalignant B cells are inclusive of one or more of memory B cells; mature B cells; and a subpopulation thereof comprising shed tumor antigen-stimulated B cells which have a cell surface-bound immunoglobulin comprising antibody against shed tumor antigen, and which can be induced to proliferate and differentiate into plasma cells which produce/secrete anti-shed tumor antigen antibody that may contribute to a promotion of tumor progression, as will be more apparent from the following embodiments.

The term "solid, non-lymphoid tumor" is used herein, for purposes of the specification and claims, to mean any primary tumor (a) of ductal epithelial cell origin, including tumors originating in the liver, lung, brain, bone marrow, adrenal gland, breast, colon, pancreas, stomach, prostate, gastrointestinal tract, or reproductive tract (cervix, ovaries, endometrium etc.); and (b) which secretes or produces shed tumor antigen (e.g., serous, or endometroid, or mucinous tumors). For the purposes of the present invention, "solid, non-lymphoid tumor" may also include melanoma.

The term "detector molecule" is used herein, for purposes of the specification and claims, to mean an affinity molecule having binding specificity for a shed tumor antigen that may include one or more of a peptide, an antibody (including fragments and derivatives thereof), a lectin (including fragments and derivatives thereof), and an aptamer, wherein the affinity molecule is bound to a detectable label such as a radioisotope or a magnetic molecule using covalent or noncovalent means. In a preferred embodiment, the detector molecule comprises a peptide. The presence of the detector molecule can be detected and localized using an instrument or probe, as will be more apparent from the following embodiments. Preferred radio-isotopes are those that emit a relatively weak gamma emission (e.g., 25–300 keV) that is detected efficiently by the instrument or probe used for detection; may be attenuated by soft tissue, thereby resulting in minimal in vivo scatter from tissue surrounding the radioactive tissue; and having a half life which permits waiting the time period necessary to establish a background level (blood circulation reduction) of radioactivity in the patient. Such radio-isotopes are known in the art to include, but are not limited to, $^{125}$I, $^{111}$In, $^{57}$Co, $^{99m}$Tc, and $^{75}$Se. An "effective amount of detector molecule" is used herein, for purposes of the specification and claims, to mean a sufficient amount of the detector molecule, which after blood circulation reduction, is able to concentrate in lymphoid tissues containing shed tumor antigen so as to be detected by the means for detecting the signal emitted by the concentrated detector molecule, as will be more apparent from the following embodiments.

The term "peptide" is used herein, for purposes of the specification and claims, to mean a molecule composed of a series of amino acid residues (from about 10 amino acids to about 300 amino acids or more) which has binding specificity for shed tumor antigen. The peptide may be derived from the amino acid sequence of a mAb or lectin (e.g., the peptide is synthesized or recombinantly produced as an amino acid sequence which is a portion of (derived from) the amino acid sequence of a mAb or of a lectin). "Binding specificity" means that the peptide (or other detector molecule) recognizes and binds specifically (vs. nonspecifically) to shed tumor antigen, and minimally (if at all) to the surface of normal (nonmalignant or nonprecancerous) cells/tissue, such that the binding specificity allows for differential detection of shed tumor antigen over normal cells/tissue. More particularly, the peptide has binding specificity (e.g., and with a binding affinity) sufficient to recognize and bind to shed tumor antigen in vivo in individuals having a pro-tumor immune response. In a preferred embodiment, binding affinities found to be suitable for in vivo applications may include binding affinities ranging from $2\times10^5$ M to $3\times10^9$ M or greater. A peptide, which exemplifies a peptide which can be used to form a detector molecule for use in the method according to the present invention, has the sequence of SEQ ID NO:1; and binds to a shed tumor antigen comprising mucin. Other peptides, that bind to tumor-derived mucin and that have been shown to be safely administered to humans, have been described previously, and include a sFv (Milenic et al., 1991, *Cancer Res.* 51:6363– 6371, and Larson et al., 1997, *Cancer* 80S:2458–2468); and αM2 (Sivolapenko et al., 1995, *Lancet,* 346:1662–1666). Lectins which have binding specificity for epitopes which may be expressed on shed tumor antigen may include one or more of Vicia Villosa lectin (binds to the Tn antigen); Carcinoscorpius rotunda cauda lectin (sialic acid binding); Sambus nigra agglutinin (recognizes sialic acid having an alpha 2,6 linkage to galactose (Gal) or galactosamine (GalNAc)); and Rana catesbeiana lectin (sialic acid binding).

The term "monoclonal antibody"(or "mAb") is used herein, for purposes of the specification and claims, to mean a human mAb, a murine monoclonal antibody, or engineered (e.g., recombinant) antibody molecules made therefrom which includes chimeric or "humanized" antibodies, or antibody fragments, having binding specificity for shed tumor antigen, as appreciated by those skilled in the art. Murine monoclonal antibodies may be made chimeric or "humanized" by replacing portions of the murine monoclonal antibody with the equivalent human sequence. In one embodiment, a chimeric antibody is constructed. The construction of chimeric antibodies is now a straightforward procedure (Adair, 1992, *Immunological Reviews* 130: 5–40,) in which the chimeric antibody is made by joining the murine variable region to a human constant region. Additionally, "humanized" antibodies may be made by joining the hypervariable regions of the murine monoclonal antibody to a constant region and portions of variable region (light chain and heavy chain) sequences of human immunoglobulins using one of several techniques known in the art (Adair, 1992, supra; Singer et al., 1993, *J. Immunol.* 150:2844–2857). Techniques for constructing chimeric antibodies (murine-human) of therapeutic potential have been described previously (see, e.g., Morrison et al., 1984, *Proc. Natl. Acad. Sci.* 81:6851–6855; Larrick et al., 1991, *Hum. Antibod. Hybridomas* 2:172–189). Monoclonal antibodies can be engineered to improve clearance from the blood circulation by removing a portion of the antibody (e.g. CH2 domain, and using a peptide bridge to link the CH1 and CH3 constant domains) using methods known to those skilled in the art (see, e.g., Slavin-Chiorini et al., 1997, *Cancer Biother. Radiopharm.* 12:305–316). The term "monoclonal antibody" also refers to a fragment of a monoclonal antibody molecule, wherein the fragment retains all or a portion of the binding function of the whole antibody molecule; i.e., $F(ab')_2$, Fab', Fab, Fv, scFV, Fd' and Fd fragments. Methods for producing the various fragments from MAbs are well known to those skilled in the art (see, e.g., Plückthum, 1992, *Immunol. Rev.* 130:152–188). For example, $F(ab')_2$ can be produced by pepsin digestion of the monoclonal antibody, and Fab' may be produced by reducing the disulfide bridges of $F(ab')_2$ fragments. Fab fragments can be produced by papain digestion of the monoclonal antibody, whereas Fv can be prepared according to methods described in U.S. Pat. No. 4,642,334. Single chain antibodies can be produced as described in U.S. Pat. No. 4,946,778. There are various mAbs known to those skilled in the art which having binding specificity for a shed tumor antigen. For example, mAbs that bind to tumor-derived mucin and have been shown to be safely administered to humans have been described previously, and include CC49 (ATCC CRL 9459; U.S. Pat. No. 5,512,443; Barbera-Guillem et al., 1998, *Am. J. Surg.,* 176: 339–343); B72.3 (ATCC HB-8108); Barbera-Guillem et al., 1998, supra); CC83 (ATCC CRL 9453; U.S. Pat. No. 5,512,443; Barbera-Guillem et al., 1998, supra); and one or more mabs against MUC1 as published by the International Workshop on Monoclonal Antibodies against MUC1 (*Tumor Biology,* 1998, 19:1–152). Aptamers can be made against shed tumor antigens or their epitopes using methods described in U.S. Pat. No. 5,789,157 (the disclosure of which is herein incorporated by reference).

The term "metastases" or "metastatic tumor cell" is used herein, for purposes of the specification and claims, to mean a metastasis from a primary tumor wherein the primary tumor is a solid, non-lymphoid tumor, as will be more apparent from the following embodiments.

The term "shed tumor antigen" is used herein, for purposes of the specification and claims, to mean a glycoprotein which:

(a) has a molecular size equal to or greater than about 100 kilodaltons;

(b) is released (e.g., shed) from a primary tumor or its metastases, thereby becoming soluble and allowing movement into lymphoid tissues regional or distal to the primary tumor or its metastases;

(c) comprises an polyvalent antigen which has repeated subunits (e.g., peptide domain and/or repeated carbohydrate chains), each subunit containing one or more epitopes;

(d) is produced by tumor cells in an underglycosylated (incompletely glycosylated) form and/or in a form of altered glycosylation as compared to the glycosylation pattern of the same molecule typically found exposed on most normal (nonmalignant or non-precancerous) cells;

(e) is capable of inducing a humoral immune response resulting in the production and secretion of anti-shed tumor antigen antibody; and (f) can interact with anti-shed tumor antigen antibody in forming immune complexes, wherein the immune complexes may bind and cross-link Fc receptors (e.g., FcγRI) present on the surface of Fc receptor-expressing cells.

With regard to the tumor antigen being soluble, the tumor antigen is noncellular ("shed") tumor antigen. Non-cellular tumor antigen comprises soluble tumor antigen that is not an integral part of a living tumor cell. Such shed tumor antigen exists in a form selected from the group consisting of free form (shed tumor antigen alone), in an immune complex form (shed tumor antigen bound to anti-shed tumor antigen antibody), in a form as presented on the surface of follicular dendritic cells (antigen presenting cells), in a form as bound to the cell surface of B cells, and as a form in tumor cell membranes existing apart from living tumor cells (i.e., soluble membrane complexes representing portions of dead tumor cells).

With regard to the shed tumor antigen with repeated carbohydrate chains containing one or more epitopes (hence, repeated epitopes), that is glycoprotein in composition, and that can interact with anti-shed tumor antigen antibody in forming immune complexes, wherein the immune complexes may bind and cross-link Fc receptors (FcR) present on the surface of FcR-expressing cells, and for purposes of illustration, and not limitation, exemplifying such shed tumor antigen are mucins and mucin-like molecules. For a review of the structure of the family of mucin molecules, see Finn et al. (1995, *Immunol. Rev.,* 145:62–89). Briefly, mucins are high molecular weight glycoproteins (e.g., greater than about 100 kiloDaltons (kD) in molecular mass) of which a significant portion of the polypeptide backbone comprises a domain composed of a tandomly repeating peptide subunits (e.g. about 20 to about 125 repeats). Mucins are found on normal ductal epithelial cells in sequestered locations that are not normally exposed to the immune system (e.g., restricted to the lumen of duct). However, in processes such as transformation (e.g, pre-cancerous) or tumor development, and due to various factors (e.g., the increased production of mucin, lack of availability of glycosyltransferases), tumor cells produce mucin in an underglycosylated (incompletely glycosylated) form and/or in a form of altered glycosylation (e.g., with a terminal sialic acid group). An immune response against tumor cell-produced mucin is thought to be primarily directed against one or more epitopes on the mucin glycoprotein which is exposed to the immune system as a result of underglycosylation or altered glycosylation. Thus, because of the underglycosylation or altered glycosylation in growing tumors, the shed tumor mucin has epitopes not normally found on mucin or not normally exposed to the immune system. Such epitopes may include, but are not limited to, carbohydrate epitopes comprising the sialyl Tn (sTn) antigen (substantially comprising the NeuAc portion of NeuAcα2→6GalNAcα1→O-Ser- or Thr); the Tn antigen (comprising the GalNAc portion of GalNAcα1→O-Ser- or Thr), the T antigen, or other sialic acid containing epitopes (e.g., substantially comprising NeuAc α2 on the carbohydrate chains (a) NeuAcα2→6Gal→-O-Ser- or Thr, (b) NeuAcα2→3Gal→O-Ser- or (c) NeuAcα2→3GalNAc→O-Ser- or Thr); or a combination thereof (e.g., comprising both the sTn antigen and Tn antigen). An example of a mucin-like glycoprotein which is differentially glycosylated by tumor cells, and is shed by tumor cells, is SSEA-1 antigen.

Tumor-associated glycoproteins, and their characterization such as nature of carbohydrate chain structure and/or monoclonal antibody binding, are known to those skilled in the art (see, e.g., Table V of Hakomori, 1989, *Adv. Cancer*

*Res.* 52:257–331). Tumor-associated glycoproteins which are known to those skilled in the art as being found in a soluble form include, but are not limited, to the human equivalents of those presented in Table 1.

TABLE 1

| Soluble-tumor Ag | Antibody | Characteristic |
|---|---|---|
| sialyl SSEA-1 ("SLX")[1] | FH-6 | pancreatic, lung, gastric, ovarian, cervical adeno-carcinomas |
| PA8-15[2] | mAb PA8-15 | pancreatic, gastro-intestinal carcinoma |
| MUSE 11[3] | mAb MUSE 11 | adenocarcinoma, pancreatic cancer |
| Her-2/neu[4] | mAb GFD-OA-p185-1 | 185 kD; various carcinomas |
| TA90[5] or U-TAA[5] | mAb ADI-40F4 | melanoma |
| KL-6 antigen[6] | mAb K1-6 | various adenocarcinomas |

[1]-Lee et al., 1992 J. Formos. Med. Assoc. 91:760–3.
[2]-Arai et al., 1990, Jpn. J. Clin. Oncol. 20:145–53.
[3]-Takai et al., 1991, Nippon Shokakibyo Gakkai Zasshi, 88:170–4
[4]-Meden and Kuhn, 1997, Eur. J. Obstet. Gynecol. Reprod. Biol. 71:173–9.
[5]-Hsueh et al., 1998, J. Clin. Oncol. 16:2913–2920; Euhus et al., 1990, Int. J. Cancer 45:1065–70.
[6]-Kohno et al., 1989, Cancer Res. 49:3412–9.

For purposes of illustration, and not limitation, in a preferred embodiment of the present invention, the shed tumor antigen comprises the gene product of the MUC-1 gene (also known as polymorphic epithelial mucin) as detected by one or more epitopes. In this preferred embodiment, the epitopes of the shed tumor antigen to which anti-shed tumor antigen-antibody are directed, include the sTn antigen, Tn antigen, or other sialic acid containing epitopes (e.g., substantially comprising NeuAcα2 on carbohydrate chains)

With regard to the humoral immune response that may be induced by the shed tumor antigen, it is known that the immune response induced by tumor cell-associated mucin is predominantly cellular (CD8+), with little or no antibody produced. In contrast to mucin bound to the surface of whole tumor cells, shed tumor mucin induces a humoral immune response that eventually results in antibody production, but not cytotoxic T cell responses (Apostolopoulos et al., 1994, *Cancer Res.* 54:5186). However, it was not known that such an immune response may promote tumor cell growth and metastasis. In that regard, it appears that shed tumor antigen may be an immunodominant tumor antigen as compared with cell-associated antigens of the tumor presented to the immune system in the process of tumorigenesis. More particularly, shed tumor antigen may induce a humoral response, the eventual result of which may be that a significant amount of the antibody response is produced against the shed tumor antigen, relative to that induced against any other single tumor cell-associated antigen ("dominant" response). The result of this specific type of immune response is a form of tolerization of the immune system to some tumor antigens other than shed tumor antigen; and hence, the inhibition of the development of an effective antitumor humoral immune response.

The term "individual" is used herein, for purposes of the specification and claims, to mean a mammal; and preferably a human; particularly an individual who is at risk of developing, or has developed, a pro-tumor immune response. An individual who is at risk of developing, or has developed, a pro-tumor immune response may include an individual having a primary tumor comprising a solid, non-lymphoid tumor and/or its metastases; an individual with a pre-cancerous condition comprising transformed (abnormal in proliferation and/or genetic makeup as compared to normal epithelial cells of the same type) cells of ductal epithelial origin which release shed tumor antigen; an individual who is at high risk (e.g., environmentally and/or genetically) for developing a solid, non-lymphoid tumor; or an individual who has been treated for a solid, nonlymphoid tumor and thereby inherently carries a risk of recurrence. In one embodiment, the method according to the present invention is intended to detect, and then surgically remove, lymphoid tissues involved in a pro-tumor immune response in an individual who is at risk for developing, or who has developed, solid nonlymphoid tumor.

The term "tumor promoting factor" is used herein, for purposes of the specification and claims, to mean one or more soluble molecules released/secreted from B cells or their progeny (plasma cells), wherein (a) tumor promoting factor comprises one or more molecules which consists primarily of an anti-shed tumor antigen antibody, but may also consist of a combination of anti-shed tumor antigen antibody and one or more cytokines; and (b) tumor promoting factor, as an IgG antibody secreted by plasma cells, binds to shed tumor antigen in forming immune complexes, wherein the immune complexes may act: on host cells which are mediators of inflammation and/or angio-genesis (e.g., granulocytes, and/or macrophages, and/or vascular endothelial cells); and/or directly (acting on the tumor cell itself) to mediate tumor progression including, but not limited to, promoting tumor growth and/or metastasis, and/or advancing stage of malignancy. Tumor promoting factor may mediate tumor progression by the formation of immune complexes which may: induce a cascade of inflammatory processes which promote tumor development; downregulate T helper cells which normally may mount an immune response against tumor cell-associated antigens, thereby inhibiting development of an antitumor immune response; inhibit tumor cell-associated antigen presentation to human tumor-specific cytotoxic lymphocytes; increase expression on primary tumor cells of cell-surface molecules which promote metastasis; cross-link Fc gamma receptors on tumor cells which may induce tumor proliferation (e.g., possibly by activating tyrosine kinase production) and/or an increase in tumor production and secretion of mucin; facilitate a local environment which mediates spread and/or development of metastases beyond the primary tumor and to lymphoid tissues regional or distal to the primary tumor; and interact with and bind to endothelial cells in promoting angiogenesis.

The term "pro-tumor immune response" is used herein, for purposes of the specification and claims, to mean an immune response induced by shed tumor antigen, wherein the immune response can promote tumor growth and metastasis. The pro-tumor immune response may involve (a) the contact or presence of shed tumor antigen in relation to the cell surface of B cells, and cell surface of follicular dendritic cells or other antigen presenting cells (e.g., contained in lymphoid tissues); (b) activation of such B cells by shed tumor antigen; and (c) induction of such B cells (or plasma cells therefrom) to secrete tumor promoting factor in sufficient amounts which may act indirectly (via immune effector cells) and/or directly (on the tumor cells) to mediate tumor progression (e.g., invasion and metastasis). Typically, foci of a pro-tumor immune response may be localized to lymphoid tissues containing shed-tumor antigen activated B cells, shed tumor antigen, and follicular dendritic cells presenting shed tumor antigen (e.g., in the form of immune complexes).

One drawback of using either radioimmunodiagnosis (RAIDS) or radioimmunoguided surgery (RIGS) to search for metastases from solid, nonlymphoid tumors is the observed false positivity (lack of demonstration of tumor cells) in draining lymph nodes. Current belief is that surgical removal of such lymph nodes presents a serious problem to general applicability of radioimmunodiagnosis and radioimmunoguided surgery since the dissection represents removal of non-neoplastic tissue (see, e.g., Stephens et al., 1993, supra). Another drawback is that radioimmunodiagnosis and radioimmunoguided surgery typically use an antibody for targeting the imaging agent to the tumor. Such antibody, when having specificity for shed tumor antigen, may cause the formation of additional immune complexes which could potentially aid tumor progression. The present invention relates to the discovery of a novel mechanism in which shed tumor antigen induces a pro-tumor immune response which can mediate tumor progression. This mechanism involves the specific type of immune response induced by shed tumor antigen. Foci of the immune cells and shed tumor antigen involved in the pro-tumor immune response are often found in lymphoid tissues wherein the detection of these involved lymphoid tissues represents some of the false positive lymph nodes described for radioimmunodiagnosis and radioimmuno-guided surgery. In a preferred embodiment of the method according to the present invention, peptides are used as detector molecules for detecting lymphoid tissues involved in a pro-tumor immune response. Peptides have one or more advantages over antibodies, wherein the one or more advantages may be selected from the group consisting of reduced immunogenicity, lack of an Fc domain, and a increased rate of bioclearance (e.g., blood pool reduction).

The method of the present invention relates to detecting the presence of shed tumor antigen in lymphoid tissues involved in a pro-tumor immune response in an individual, and therapeutically treating the individual by surgically removing those lymphoid tissues detected. In this method, after detecting lymphoid tissue containing shed tumor antigen, all of the detected lymphoid tissue, or that portion of the lymphoid tissue containing shed tumor antigen, is surgically resected. By surgically resecting the lymphoid tissue, removed from the individual is one or more of localized: shed tumor antigen; shed tumor antigen-activated B cells; and follicular dendritic cells presenting shed tumor antigen. A therapeutic effect resulting from surgically resecting such lymphoid tissue (e.g., false positive lymph nodes) would be an unexpected result, as the current view is that such surgical resections do not benefit the patient, but instead increases morbidity (Stephens et al., 1993, supra). Additionally, a therapeutic effect resulting from surgically resecting lymph nodes regional to a primary tumor to prevent tumor growth and progression is an unexpected result in view of the belief by those skilled in the art that regional lymph nodes play an important role in the development of tumor immunity (Fisher and Fisher, 1971, *Cancer,* 27:1001–04); and that regional lymph nodes are of primary importance in the maintenance of tumor immunity (Fisher and Fisher, 1972, *Cancer,* 29:1496–1501).

Figure 7:
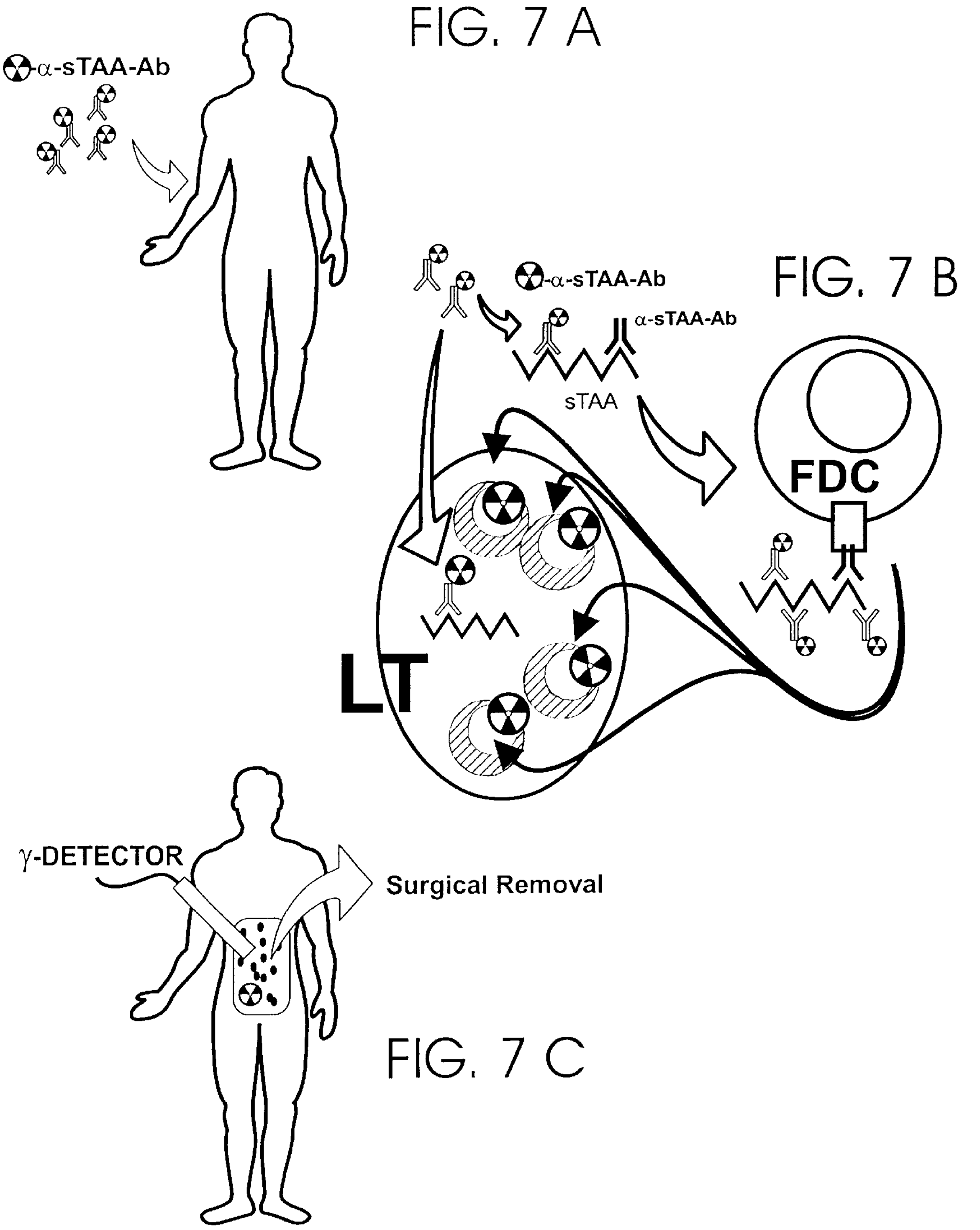
FIG. 7A is an illustration of a labeled detector molecule ("sTAA Ab") having binding specificity for the shed tumor antigen ("sTAA") involved in the pro-tumor immune response.
FIG. 7B is an illustration showing the time interval between administration (FIG. 7A) and surgery (FIG. 7C), wherein the detector molecule localizes into lymphoid tissue ("LT") containing sTAA, which are a foci of a pro-tumor immune response, if present.
FIG. 7C is an illustration showing a surgical procedure in which the individual is scanned for lymphoid tissue containing localized deposits of sTAA, which are then surgically removed.

The present invention also comprises methods for detecting a specific type of immune response or process (collectively referred to hereinafter as "immune response") in a tumor bearing individual, wherein this specific type of immune response promotes tumor development and progression as will be more apparent from the following illustrative embodiments. In a preferred embodiment, the shed tumor antigen is mucin-1 (polymorphic epithelial mucin). In one illustration of a method for detecting the presence or absence of a pro-tumor immune response according to the present invention, an effective amount of detector molecule having binding specificity for shed tumor antigen is administered to the individual (FIG. 7A). As appreciated by those skilled in the art, an effective amount of detector molecule will vary depending on such factors which include, but are not limited to, the type and nature of detector molecule label used (e.g., a radioisotope, and the emission of the isotope; the size, type, and strength of emission from, a magnetic molecule), the efficiency of attaching the affinity molecule to the detectable label in forming a detector molecule, the binding specificity and affinity of the detector molecule for shed tumor antigen, and the efficiency of the individual'bioclearance of the detector molecule (e.g., blood circulation reduction). For purposes of illustration, and not limitation, a minimum detectable radioactive signal from detector molecule containing $^{125}$I is approximately 10 counts/second; and a minimum amount of radioactivity detectable when scanning continuously is approximately 3 nanoCuries (nCi). After administration of the detector molecule, the individual is then subjected to a time interval sufficient for allowing the detector molecule to localize and concentrate in lymphoid tissue containing shed tumor antigen, and also allowing for unbound detector molecule (e.g., detector molecule not specifically bound to shed tumor antigen) to clear from the individual'system (e.g., blood circulation reduction) thereby achieving a background level of signal emitting or resonating from nonspecifically bound detector molecule (FIG. 7B). In general, and depending on the detector molecule used, a time period could vary from hours up to two weeks after administration of the detector molecule to achieve sufficient clearance of radioactivity from the blood circulation when using a detector molecule which is radiolabeled. However, as appreciated by those skilled in the art, such a time period may be shorter or longer depending on several parameters including, but not limited to, circulating immune complex formation, kinetics of tumor antigen shedding, chemical properties (e.g., solubility, hydrophobicity, etc.) of the affinity molecule utilized in making the detector molecule, and clearance properties of the detector molecule. After such a time period, the individual to whom is administered is then accessed by exploratory surgery, and probed or scanned for identifying and localizing lymphoid tissues containing shed tumor antigen by using an instrument or probe capable of distinguishing and localizing the signal from the detector molecule bound to shed tumor antigen. The instrument or probe is positioned adjacent to the lymphoid tissue, wherein if shed tumor antigen is detectably present in that lymphoid tissue, a signal of measurably greater intensity or strength than that of the background level is detected. The finding of lymphoid tissue detected as containing shed tumor antigen is an indicator of the presence of a pro-tumor immune response in the individual. In a method of immune corrective surgery according to the present invention, the same procedure is followed (for detecting lymphoid tissue containing shed tumor antigen), but the method of immune corrective surgery further includes surgically resecting all or that portion of the lymphoid tissue detected as containing shed tumor antigen (FIG. 7C). The same area from which the lymphoid tissue was removed may be rescanned using the probe to confirm that the lymphoid tissue detected as containing shed tumor antigen has been completely removed, or alternatively, that a second source of lymphoid tissue, located directly below the space from which was removed the initial lymphoid tissue, is not the source for all or a portion of the detected signal (representing the presence of shed tumor antigen). Thus, the rescanning ensures that all lymphoid tissue detected by the probe or instrument as containing shed tumor antigen, and which exhibits a signal of measurably greater intensity or strength than that of the background level, may be detected and then surgically removed. For purposes of illustration, a "signal of measurably greater intensity of strength than that of the background level" is a signal greater or equal to the background signal plus 3 standard deviations.

For purposes of the description, the methods of the present invention will be illustrated in the following examples.

EXAMPLE 1

This example, and other Examples herein, provide evidence of the B cell involvement, and the specific type of immune response to shed tumor antigen in lymphoid tissues, which are involved in a pro-tumor immune response that promotes tumor progression and metastasis. For this Example, and Examples 2 and 3, it is important to consider the following concept. Various strains of mice were used as a standard animal model for evaluating whether a germinal center B cell response may be involved in tumor progression, including promoting metastasis. In the tumor bearing mice of B cell competent strains, a similar germinal center B cell response was observed in lymph nodes regional to a primary tumor as observed in tumor bearing humans. In that regard, and to assess whether B cells are effector cells of, at least in part, a tumor promoting immune response, an in vivo standard experimental model was used. To determine whether different populations of B lymphocytes could influence tumor progression in vivo, C3H mice were injected in the mammary pad with $1\times10^6$ Met 129 (high mucin-secreting mammary tumor) cells. Tumor growth in CH3 mammary gland tumor-bearing mice was compared when the mice were injected every 2 days for a 14 day period with either B lymphocytes (50,000 cells) isolated from normal mouse spleen, B lymphocytes isolated from lymphoid tissues (e.g., spleens) of tumor bearing mice (50,000 cells), or 50,000 B lymphocytes isolated from tumor tissue (B-TIL) of tumor bearing mice. The various B cell populations were isolated using magnetic beads having anti-CD19 mAb bound thereto. After the 14 day period, liver metastasis and spleen tumor growth (tumor+metastasis score) was evaluated. As shown in FIG. 1, B lymphocytes from lymphoid tissue of tumor bearing mice ("T-Spl") and B-TIL each promoted statistically significant tumor growth and metastasis in vivo, whereas B lymphocytes from normal spleen ("N-Spl") did not enhance either tumor growth or metastasis. A conclusion that can be drawn from these results is that to gain the ability to promote tumor progression, B lymphocytes contained in lymphoid tissues must first be exposed to shed tumor antigen.

Figure 2:
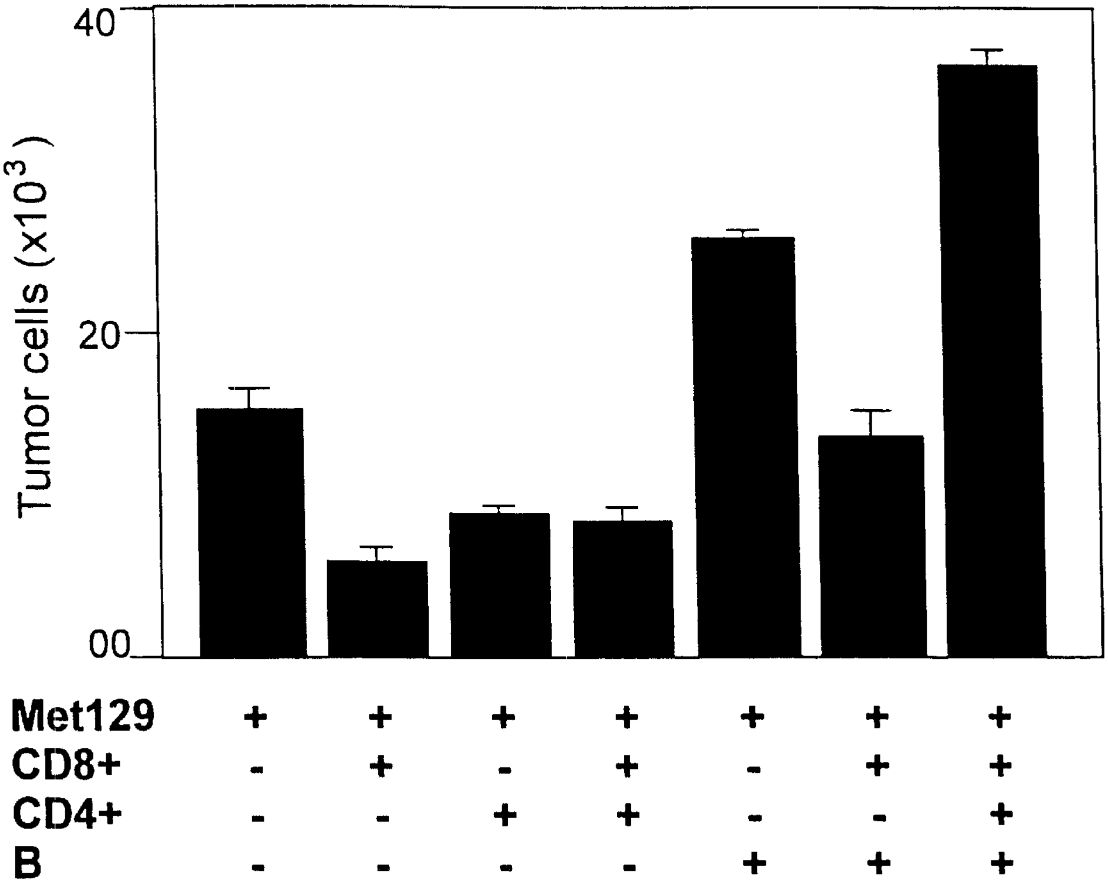
FIG. 2 is a bar graph illustrating in vitro tumor growth of Met 129 tumor cells alone; or co-incubated with either CD8+ cells, CD4+ cells, CD8+ cells and CD4+ cells, B cells from tumor bearing mice ("B"), CD8+ cells and B, or B and CD8+ cells and CD4+ cells.

The following experiment illustrates that B cell promotion of tumor progression in vitro can be mediated via a direct action by B cells that does not require a T cell intermediary response; but may also act synergistically with CD4+ T cells, when present. In this illustration, several populations of lymphocytes were isolated using magnetic bead separation techniques from Met 129 tumors removed from C3H mice. The lymphocyte populations included B cells isolated from tumor bearing mice, CD4+ lymphocytes isolated from tumor bearing mice, and CD8+ lymphocytes isolated from tumor bearing mice (CD8+). Ten thousand Met 129 cells were cultured in 1.5 ml of tissue culture medium supplemented with 10% fetal bovine serum (FBS) per well in 24 well plates alone, or in the presence of either 10,000 CD8+ cells, in the presence of 10,000 CD4+ cells, in the presence of 10,000 CD8+ cells and 10,000 CD4+ cells, in the presence of 10,000 B cells, in the presence of 10,000 B cells and 10,000 CD8+ cells, or in the presence of 10,000 CD8+ cells, 10,000 CD4+ cells and 10,000 B cells. After 72 hours of co-incubation in monolayer culture, Met 129 tumor cell growth was quantitated using Alcian blue staining; e.g., adherent mucin-producing cells (Met 129 tumor cells) were counted. As shown in FIG. 2, CD8+ cells co-incubated with Met 129 (Met 129+, CD8++, CD4+–, B–) resulted in a statistically significant reduction in tumor cell growth, and thus appeared to effect Met 129 tumor cell death when compared to the control of Met 129 alone (Met 129+, CD8+–, CD4+–, B–) Likewise, a slight reduction in tumor growth or no increase in tumor growth, as compared to the control, was observed when Met 129 tumor cells were co-incubated with either CD4+cells (Met 129+, CD8+–, CD4++, B–), in the presence of CD8+ cells and CD4+ cells (Met 129+, CD8++, CD4++, B–), or in the presence of B cells and CD8+ cells (Met 129+, CD8++, CD4+–, B+). In contrast, statistically significant increased tumor cell growth was observed when B cells were co-incubated with Met 129 tumor cells (FIG. 2: Met129+, CD8+–, CD4+–, B+), and when CD8+ cells, CD4+ cells and B cells were co-incubated with Met 129 tumor cells (FIG. 2: Met 129+, CD8++, CD4++, B+), as compared to growth of the control of Met 129 tumor cells alone (Met 129+, CD8+–, CD4+–, B–).

In summary, these results indicate that B cells alone can promote tumor progression via a direct action by B cells that does not require a T cell intermediary response (FIG. 2: Met 129+, CD8+–, CD4+–, B+).

EXAMPLE 2

In this illustration, shown is that a process that depletes B cells can also affect tumor progression in tumor bearing animals. Fifty three C3H mice were injected intrasplenically with $10^6$ Met 129 tumor cells. The injected mice were then divided into two treatment groups. One group of 28 mice was injected with an irrelevant (not directed against any specific mouse antigen) goat IgG antibody (170 $\mu$g per injection) at days 5, 7, and 9 following tumor challenge. A second group consisted of 25 mice injected with goat anti-mouse IgG and goat anti-mouse IgM (170 $\mu$g per injection) at days 5, 7, and 9 following tumor challenge. The goat anti-mouse IgG and IgM was used to deplete the C3H mice of their B cells, thereby interrupting the host B cell-mediated pro-tumor immune response. At 22 days following tumor challenge, the two groups of mice were analyzed for primary tumor growth in the spleen, metastasis to the liver, and extra-regional metastasis (abdominal lymph nodes). Table 2 shows one experiment in which compared was primary tumor growth, and the incidence of liver metastasis ("Liver Met.") and extra-regional metastasis ("Extra-R Met.") in the mice treated with irrelevant goat IgG ("Goat-IgG"), and mice treated with goat anti-mouse IgG and goat anti-mouse IgM ("Anti-IgG Anti-IgM"). Table 2 shows that there is a statistically significant reduction in the incidence of metastasis in B cell-depleted mice ("Anti-IgG Anti-IgM") as compared to the control group receiving irrelevant IgG.

TABLE 2

| Observed | Goat-IgG Control | Anti-IgG Anti-IgM |
|---|---|---|
| Tumor | 8 of 8 | 6 of 6 |
| Liver Met. | 5 of 8 | 0 of 6 |
| Extra-R Met. | 6 of 8 | 0 of 6 |

Figure 3:
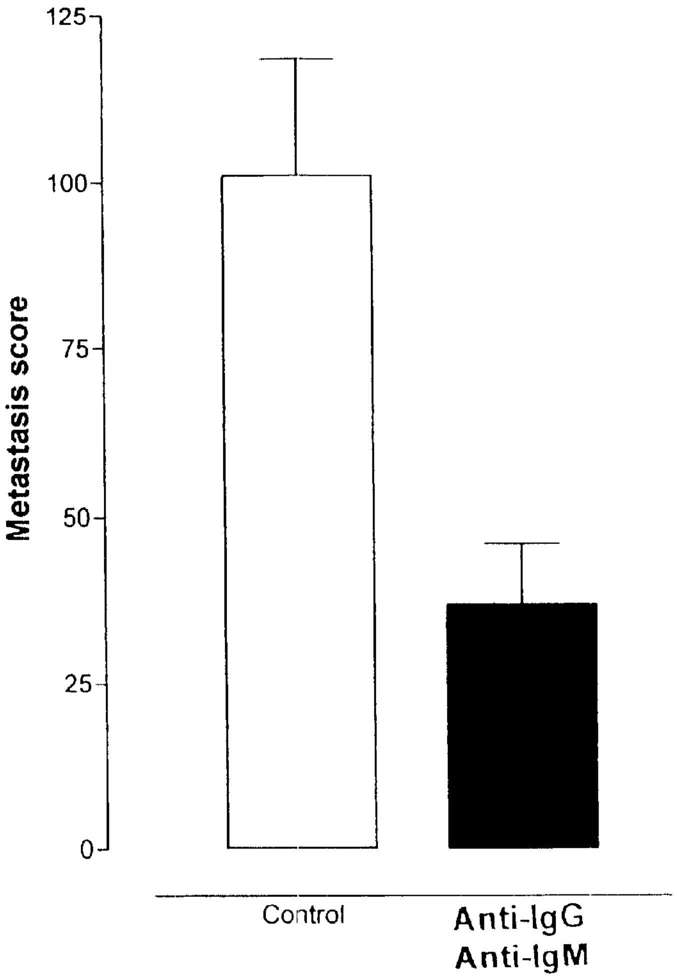
FIG. 3 is a bar graph illustrating the extra-regional (lymph node) and liver metastases scores (combined as "metastasis score") in mice treated with either irrelevant goat IgG, or in mice having B cells depleted ("Anti-IgG").

Spleen tumor was scored and compared among the two groups of mice. Treatment of the tumor bearing mice with either goat IgG, or goat anti-mouse IgG and goat anti-mouse IgM, had little effect on the growth of the primary tumor in the spleens. In contrast, as shown in FIG. 3, mice in which B cells were depleted ("Anti-IgG") showed a statistically significant reduction in the incidence of extra-regional metastasis and liver metastasis as compared to the extra-regional metastasis and liver metastasis exhibited by the control group of mice treated with irrelevant goat IgG. The results in FIG. 3 are normalized values from two experiments. It is important to note that at least 50% of the mice having B cells depleted, did not develop detectable metastases.

In summary, the results illustrated in Table 2, and FIG. 3 further support the finding that a host B cell response (pro-tumor immune response) is required for statistically significant promotion of tumor invasion and metastasis. Such host B cells may include those present in lymphoid tissues involved in a pro-tumor immune response, as detected by a detector molecule for the presence of shed tumor antigen, wherein such B cells have been activated by shed tumor antigen. Additionally, the results illustrated in Table 2, and FIG. 3 further support a method for depleting B cells which are involved in the progression of solid, nonlymphoid tumors by surgically removing lymphoid tissues involved in a pro-tumor immune response in a tumor bearing individual, or in an individual having a pro-tumor immune response.

EXAMPLE 3

Figure 4A:
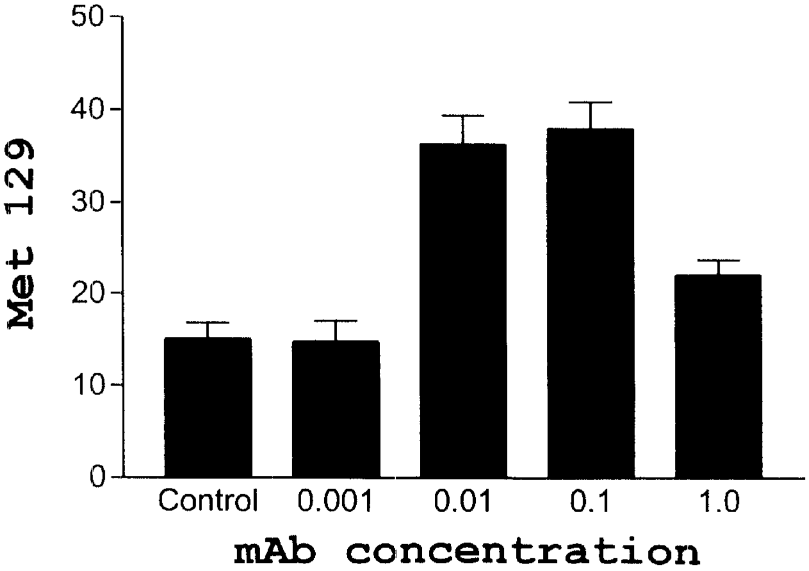
FIG. 4A is a bar graph of induction of Met 129 tumor cell growth in relation to concentration of added anti-shed tumor antigen antibody (in presence of shed tumor antigen).
Figure 4B:
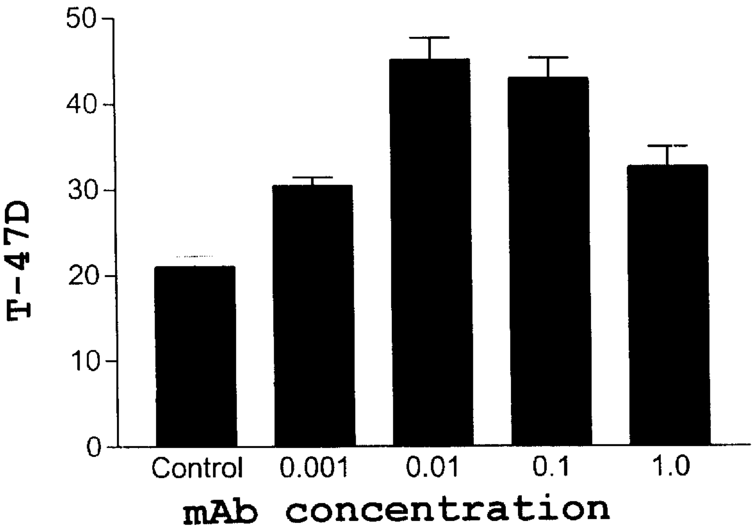
FIG. 4B is a bar graph of induction of T-47D tumor cell growth in relation to concentration of added anti-shed tumor antigen antibody (in presence of shed tumor antigen).

In this Example, illustrated is the ability of immune complexes consisting of shed tumor antigen and ant-shed tumor antigen antibody to promote tumor progression. In one aspect, immune complexes comprising anti-shed tumor antigen mAb and shed tumor antigen were shown to induce tumor cell growth. In this in vitro tumor cell proliferation assay, separately used were mucin-secreting tumor cell lines T-47D (human breast carcinoma) and Met129 (murine mammary carcinoma). The tumor cells were aliquoted into wells of a 96 well plate at 1000 cells per well for a total of 30 wells per cell line. Immediately following the seeding of the tumor cells, a concentration (either 0.001, 0.01, 0.1 and 1.0 μg) of dialyzed anti-sTn mAb or control medium was added to each well. After incubating the plates for approximately 72 hours at 37° C. in 5% $CO_2$, proliferation was assessed by counting adherent cells in each well. As shown in FIGS. 4A and 4B, anti-shed tumor antigen antibody (e.g., anti-sTn mAb), in the presence of shed tumor antigen (mucin) can promote growth of shed tumor antigen-secreting tumor lines. More particularly, the dependence on concentration of the anti-sTn mAb is characteristic of immune complex mediation of tumor growth; i.e., tumor growth is promoted most in conditions lacking antigen excess and antibody excess. Immune complex mediation of a pro-tumor immune response has also been confirmed by immunohisto-chemical analysis for shed tumor antigen and anti-shed tumor antigen antibody in tissue sections from standard animal models for tumor invasion and metastasis.

Figure 5:
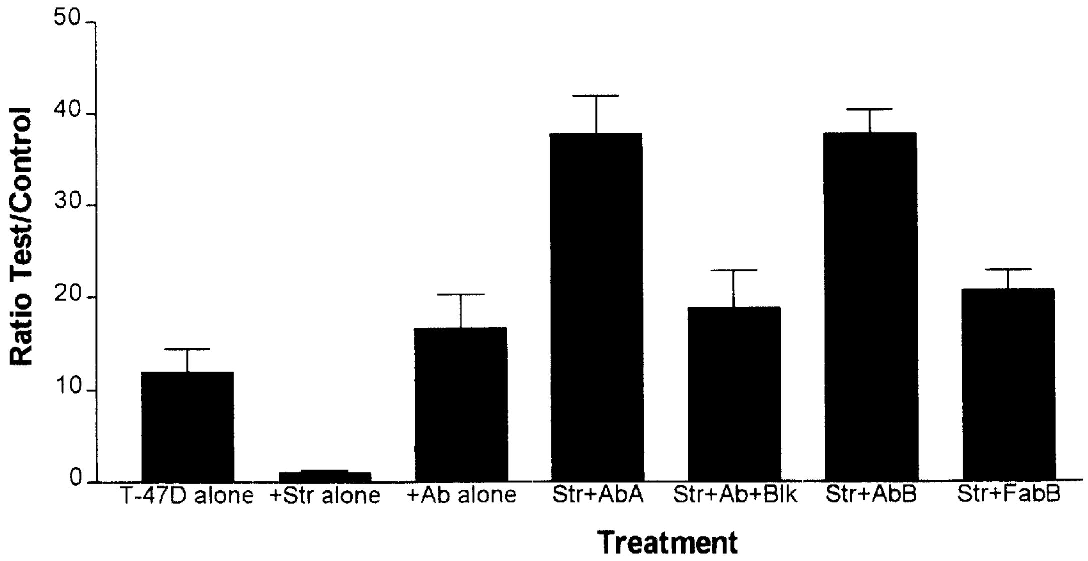
FIG. 5 is a bar graph illustrating invasion of shed tumor antigen-secreting tumor cells through matrix when incubated with various cellular components, antibodies, or antibody fragment.

In another aspect, immune complexes comprising anti-shed tumor antigen mAb and shed tumor antigen were shown to induce tumor cell invasion in the presence of murine stromal cells (granulocytes, macrophages, fibroblasts, and endothelial cells). In this in vitro tumor cell invasion assay, used were mucin-secreting human tumor cell line T-47D, a Boyden chamber, and a commercially available basement membrane matrix preparation ("matrix"). In this assay, tested was the ability of tumor cells ($2\times10^4$ cells) to migrate through the matrix in the following conditions: matrix alone; matrix containing stromal cells ($2\times10^5$ cells); matrix in the presence of anti-sTn mAb (0.06 μg); matrix containing stromal cells in the presence of anti-sTn mAb; and matrix containing stromal cells in the presence of Fab fragments of the anti-sTn mAb. The plates were incubated at 37° C. in 5% $CO_2$, and fresh media (with or without antibody, depending on the condition) was substituted every 24 hours. Invasion was measured by counting the number of tumor cells per well which migrated to the bottom of the chamber after 48 to 72 hours. FIG. 5 shows that the maximum invasion through the matrix was observed when the shed tumor antigen-secreting tumor cells were incubated in the presence of stromal cells and either of two anti-sTn mAb tested ("Str+AbA"; and "Str+AbB") as compared to tumor cells alone ("T-47D alone"), or stromal cells ("+Str alone"), or anti-sTn mAb ("+Ab alone), or stromal cells in the presence of Fab fragments of the anti-sTn mAb (Str+FabB). These experiments are further evidence that shed tumor antigen secreted by tumor cells can interact with anti-shed tumor antigen antibody in forming complexes that can activate cells, such as granulocytes and macrophages, to secrete enzymes and factors (e.g., tissue degrading enzymes) that promote tumor progression. The involvement of immune complexes, as opposed to the action of antibody alone, was confirmed by using a tumor cell which did not produce sTn-containing shed tumor antigen; i.e., when such tumor cells were incubated in the presence of stromal cells and anti-sTn mAb, there was no increase in tumor invasion as compared to the control values.

EXAMPLE 4

This Example illustrates that shed tumor antigen is present in lymph nodes determined to be "false positive" during a procedure such as radioimmunoguided surgery. Forty colorectal carcinoma patients in a radioimmunoguided surgery protocol (using the methods outlined in U.S. Pat. No. 4,782,840) were assessed for the anatomical distribution of detector antibody comprising radiolabelled anti-mucin-1 monoclonal antibody. Positive detection (a signal of measurably greater intensity of strength than that of the background level of detector antibody) localized in the tumor, and also in abdominal lymph nodes, but not in a random distribution. All specimens, whether positive or negative by radioimmunoguided surgery, were examined histopathologically including histological staining (hematoxylin, eosin, and mucicarmine) using methods known in the art. The distribution of positive lymph nodes (which include false positives) are shown in Table 3, wherein+LN means lymph node positive for mucin-1, and as expressed relative to the number of patients assessed.

TABLE 3

| Stage | Upper Abdomen +LN | Middle Abdomen +LN | Lower Abdomen +LN | Regional +LN | Peri-pheral +LN |
|---|---|---|---|---|---|
| Stage I&II | 15/21 | 11/21 | 1/21 | 3/21 | 0/21 |
| Stage III | 16/19 | 14/19 | 6/19 | 9/19 | 0/19 |

By histologically staining of the lymph node specimens, it was determined that at least 80% of the positive lymph nodes did not contain evident tumor cells, but did contain shed tumor antigen in the germinal centers in a distribution consistent with presentation by follicular or germinal center dendritic cells. Additionally, the germinal centers of those positive lymph nodes always showed an intense B cell response. As to patients with either Stage I or Stage II disease, all of the positive lymph nodes lacked evident tumor cells. This is consistent with the definition of Stage I and Stage II disease in that evident tumor has yet to invade, or has very limited invasion into (i.e., only attachment to) surrounding tissues. However, shed tumor antigen would have more than ample opportunity to migrate into, and deposit in, surrounding tissues and distal tissues during Stage I or Stage II disease.

EXAMPLE 5

This Example illustrates an embodiment of the immune corrective procedure according to the present invention using a detector molecule. It will be appreciated by those skilled in the art that based on the following results, an effective amount of detector molecule (e.g., selected from the group consisting of a mAb, lectin, peptide or aptamer) may also be used effectively in the detection of shed tumor antigen-containing lymphoid tissues for surgical removal according to the method of the present invention. Immune corrective surgery according to the present invention may be used by itself, in conjunction with chemotherapy or radiotherapy, in conjunction with traditional surgical techniques, or in conjunction with radioimmunoguided surgery. In this illustration, immune corrective surgery was used in addition to radioimmunoguided surgery. Using $^{125}$I anti-mucin-1 mAb as the detector molecule for detecting localization of shed tumor antigen (mucin) in lymphoid tissues, a prospective clinical trial was performed with the following objective: to find, in a tumor bearing individual, lymphoid tissue containing shed tumor antigen; to remove from the tumor bearing individual such lymphoid tissue detected; and to postoperatively monitor the treated individual for survival from neoplastic disease.

In that regard, areas of lymphoid tissue not containing obvious tumor, as determined by palpation and inspection, but which showed increased radioactivity ($\geqq$20 counts per 2 seconds using a hand-held gamma detecting probe) when compared to adjacent areas of tissue with less radioactivity (<20 counts per 2 seconds), and which were in the general anatomic area of a tumor, were resected at the discretion of the surgeon. Post-operative follow-up included the evaluation of the clinical status and survival of individuals undergoing such treatment as compared to the clinical status and survival of individuals in which the detected lymphoid tissues practically could not be, or electively were not, resected.

Briefly, procedures for this clinical trial are as follows. Tumor bearing individuals having primary or recurrent colorectal carcinoma were selected. Anti-mucin-1mAb was labeled using sodium iodide $^{125}$I using the 1,3,4,6 -tetrachloro-3-alpha-diphenylglycouril method. Radiolabeled mAb was then purified by chromatography, and sterilized by filtration. $^{125}$I anti-mucin-1 mAb was then prepared in phosphate buffered saline in producing the detector molecule. Prior to administration of the detector molecule, multiple doses of a saturated solution of potassium iodide (e.g., 1 ml of a 500 mg/ml solution of KI) were given to the individual to block thyroid uptake of the detector molecule. Detector molecule (e.g., ranging from 0.2 mg to 10 mg) was administered intravenously. In a time period sufficient to establish a background level of radioactivity in the individual (e.g., about 21 days to about 28 days post-injection for a whole mAb), the individual underwent exploratory surgery in which a hand-held gamma detecting probe was used to detect radioactive lymphoid tissue (for immune corrective surgery). Each of the two groups of tumor-bearing individuals, having colorectal carcinomas homogenous in tumor staging, were surgically treated under a different protocol. A first treatment group comprised 34 patients who were subjected to radioimmunoguided surgery alone. This first treatment group included 9 stage I (AJCC staging) patients, 12 stage II patients, and 13 stage III patients. A second treatment group comprised 24 patients were treated with immune corrective surgery according to the present invention, and then also subjected to radioimmunoguided surgery. This second treatment group included 5 stage I patients, 6 stage II patients, and 13 stage III patients. For each group, radioimmunoguided surgery was performed to remove neoplastic tissue using a protocol as essentially described previously (see, e.g., U.S. Pat. No. 4,782,840).

Figure 6:
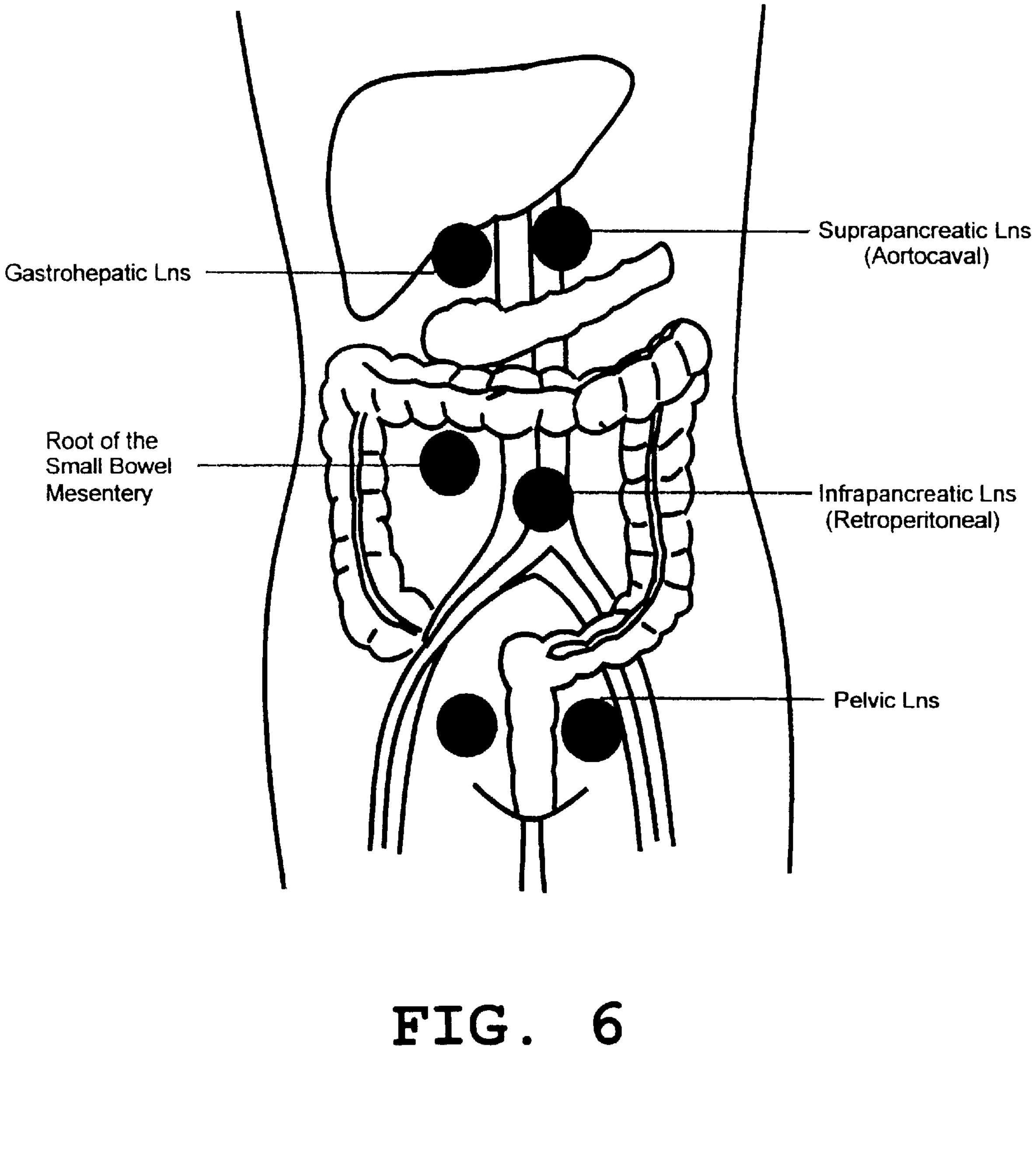
FIG. 6 is a graphic representation comprising a map of the approximate location of lymphoid tissues, including abdominal lymphoid tissues ("Lns"), in an individual.

In the immune corrective surgery according to the present invention, lymphoid tissues containing shed tumor antigen (as detected by the detector molecule) were removed from one or more of the areas selected from the group consisting of the gastrohepatic ligament, celiac axis, iliac vessels, retroperitoneum, or a combination thereof; areas or sites from which a surgeon would not traditionally remove tissue without obvious tumor. FIG. 6 provides a "lymphoid tissue" map which may be used to assist in identifying some of the lymphoid tissues contained with the abdominal region which may be frequently involved in a pro-tumor immune response as found using an effective amount of detector molecule to detect shed tumor antigen in the method according to the present invention. After resection of the lymphoid tissues detected as containing shed tumor antigen, the areas around the excised lymphoid tissues were rescanned for residual radioactivity. The five year survival rate (free of clinically evident neoplastic disease) was calculated for each treatment group, and expressed as a percentage (Table 4, "5 yr."). Table 4 shows a comparison of the 5 year survival rate between colorectal tumor bearing individuals undergoing tumor removal by radioimmunoguided surgery only ("Group 1"); colorectal tumor bearing individuals undergoing immune corrective surgery according to the present invention to remove lymphoid tissues involved in a pro-tumor immune response, in addition to undergoing tumor removal by radioimmunoguided surgery ("Group 2"); and as compared to outcomes of traditional (standard) surgery for colorectal tumor bearing individuals as reported by the National Cancer Database ("T.Surg."). As shown in Table 4, tumor bearing individuals who received immune corrective surgery according to the present invention to remove lymphoid tissues containing shed tumor antigen, in addition to tumor removal by radioimmunoguided surgery, showed a statistically significant increase in 5 year survival as compared to tumor bearing individuals receiving either radioimmunoguided surgery alone, or traditional surgery alone. Of particular note is the significant improvement in 5 year survival for patients who had stage III (regionally disseminated) disease at the time of immune corrective surgery according to the present invention. In summary, the results in Table 4 clearly show that by not removing lymphoid tissue containing shed tumor antigen, patients' 5 year survival rates are statistically reduced (as compared to that of patients from which lymphoid tissue containing shed tumor antigen had been removed using the method according to the present invention).

TABLE 4

| Patients | # of patients | Stage | 5 yr. |
|---|---|---|---|
| Group 1 | 9 | I | 67% |
| Group 2 | 5 | I | 100% |
| T.Surg. | — | I | 68% |
| Group 1 | 12 | II | 42% |
| Group 2 | 6 | II | 100% |
| T.Surg. | — | II | 64% |
| Group 1 | 13 | III | 31% |
| Group 2 | 13 | III | 77% |
| T.Surg. | — | III | 44% |

Using the procedures in this illustration, an effective amount of detector molecule having binding specificity and affinity for a shed tumor antigen may be used to target and detect shed tumor antigen in lymphoid tissues involved in a pro-tumor immune response. Detection of lymphoid tissue containing shed tumor antigen by using the detector molecule is a prognostic indicator that an individual has an immune response (pro-tumor immune response) which can promote tumor progression (e.g., one or more of growth, invasion, and metastasis). As appreciated by those skilled in the art, the amount of detector molecule injected, and the time period sufficient to establish a background level of radioactivity (or signal) in the individual may vary depending on factors that may include the binding affinity and specificity of the detector molecule for shed tumor antigen, the efficiency of labeling the detector molecule with the detectable label, molecular size of the detector molecule, and clearance properties of the detector molecule. One skilled in the art would be able to determine an effective amount of detectable molecule to be administered. For purposes of illustration, but not limitation, an effective amount of detector molecule may be determined by a medical practitioner to be in a range of from about 1 $\mu$g/kg body weight to 1 mg/kg body weight or more.

EXAMPLE 6

This Example illustrates an embodiment of the immune corrective procedure according to the present invention using a detector molecule, wherein the detector molecule is preferably a peptide labeled with a detectable label. It will be appreciated by those skilled in the art that based on the results in Example 5 herein, that an effective amount of detector molecule comprising a peptide may also be used effectively in the detection for removal of shed tumor antigen-containing lymphoid tissues according to the method of the present invention. It was not known at the time of the invention that a detector molecule comprising a mAb may actually promote tumor progression, if it binds with shed tumor antigen to form immune complexes (see, e.g., FIGS. 4A, 4B, and 5). Thus, an unexpected benefit of a detector molecule comprising a labeled peptide, as compared to a detector molecule comprising a labeled antibody, is that the peptide lacks an Fc domain, thereby avoiding cross-linking of Fc receptors on either tumor cells and/or stromal cells or other Fc receptor bearing cells.

In one illustration, the method according to the present invention involves the administration (e.g., bolus intravenous or parenteral injection) to an individual of an effective amount of detector molecule comprising the peptide identified by amino acid sequence, SEQ ID NO:1. The term "parenteral" includes administration intravenously (a preferred embodiment), but also may include intramuscularly, subcutaneously, rectally, vaginally, intra-lymphatic, or intraperitoneally. The peptide is labeled with $^{125}$I using a method known in the art (e.g., iodination reaction), purified, and then prepared in dosage form. In this illustration, a saturated potassium iodide solution is administered prior to administration of the detector molecule, and until surgery is completed, in an amount sufficient to substantially block thyroid uptake of the detector molecule. An effective amount of the detector molecule is administered intravenously to the individual. In a preferred embodiment, an effective amount of the detector molecule may be an amount in the range of from about 1 $\mu$g/kg body weight to about 25 $\mu$g/kg body weight. After a time period (from the time of administration of the detector molecule) sufficient to establish a background level of radioactivity in the individual (e.g., a time period selected from the group consisting of a time period in the range of about 6 hours to about 96 hours, less than 48 hours, less than 72 hours, and less than 96 hours, post-injection), the individual undergoes exploratory surgery in which a hand-held gamma detecting probe was used to detect radioactive lymphoid tissue (lymphoid tissue containing detector molecule bound to shed tumor antigen). In the immune corrective surgical method according to the present invention, lymphoid tissues containing shed tumor antigen (as detected by the detector molecule) are removed; e.g., tissues which a surgeon would not traditionally remove without evident tumor. Optionally, after resection of the lymphoid tissues detected as containing shed tumor antigen, the areas around the excised lymphoid tissues may be rescanned for residual radioactivity and for removal of lymphoid tissue (containing shed tumor antigen) detected as the source of the residual radioactivity.

EXAMPLE 7

In this embodiment, some additional considerations are provided for instruments or probes useful for detecting the detector molecule in performing the immune corrective surgical method according to the present invention. Probes and instruments which may be useful with the methods of the present invention include, but are not limited to, a handheld probe, a laparoscopic probe, a colonoscopic probe, a gamma emission imaging instrument (e.g., gamma camera), a probe detecting a magnetic field, and a magnetic emission imaging instrument. Desirable features of the instrument or probe include, but are not limited to, dimensions, maneuverability, and composition suitable for the intended application (e.g, hand-held versus laparoscopic); a detecting means capable of detecting the signal emitted by the detector molecule, where detecting means may be controlled to detect a threshold level of signal (e.g., signal measurably greater than the background level), and may be modified to collimate the field of detection for precisely locating the source of the emitted signal; a converting means to convert the detected signal (e.g., measurably greater than background signal) to a transmission perceptible to the user (e.g., visual and/or audio); the ability to be sterilized if the probe is used within a body cavity; and a power source. As appreciated by those skilled in the art, additional design features may be incorporated depending on the intended application.

In regards to detection of radioactive emissions from an effective amount of detector molecule comprising a radiolabeled detector molecule, there are commercially available gamma probes which may be utilized with the immune corrective surgical method according to the present invention. Hand-held gamma probes are known those skilled in the art (see, e.g., U.S. Pat. No. 4,782,840, U.S. Pat. No. 5,070,878, and U.S. Pat. No. 5,383,456) to include, but are not limited to, cadmium telluride probes, cadmium telluride alloy probes, sodium iodide probes, and the like. Laparoscopic probes and camera, also known to those skilled in the art (see, e.g., U.S. Pat. No. 5,383,456), may be used in the immune corrective surgical method according to the present invention. Gamma cameras are known in the art to include a scintillation crystal or detector responsive to radiation stimuli in human glands or organs (see, e.g., U.S. Pat. Nos. 5,689,116 and 5,677,535). A gamma-detecting endoscopic probe has been described previously (see, e.g., U.S. Pat. No. 4,932,412) which can be inserted through an orifice such as the vagina or rectum for use in a body cavity to detect lymphoid tissues containing radiolabeled detector molecule bound to shed tumor antigen. These gamma cameras and endoscopic probes may be used in the immune corrective surgery according to the present invention.

As appreciated by those skilled in the art, to use an instrument or probe, the detector portion of the instrument or probe is positioned sufficiently adjacent to lymphoid tissue (scanning) so as to detect any detectable signal (e.g., radioactivity) emitted; wherein if shed tumor antigen is detectably present in the lymphoid tissue being scanned, a signal of measurably greater intensity or strength than that of the background level is detected, and subsequently the lymphoid tissue detected as containing shed tumor antigen is surgically removed. As will be appreciated by those skilled in the art, in the process of localizing and identifying lymphoid tissue containing shed tumor antigen, the distance between the instrument or probe and the lymphoid tissue being scanned will depend on several factors including, but not limited to, the intensity and pattern of the signal emitted by the detector molecule, the sensitivity of the instrument or probe in detecting the signal emitted by the detector molecule, and the level and distribution of background signal. In general, when using a hand-held cadmium telluride gamma probe to detect the radioactive signal emitted by a detector molecule (e.g., comprising $^{125}$I labeled peptide having binding specificity for mucin-1), the distance between the probe detector window and the lymphoid tissue being scanned is the operable range of about 0 cm to about 1 cm. The probe detector window is the surface area of the detecting means (e.g. cadmium telluride crystal), which is used to detect the signal emission of the detector molecule.

For example, using a laparoscopic probe to detect shed tumor antigen containing-lymphoid tissues in the peritoneal cavity, the individual is administered (via blood vessels or lymphatic system using methods known to those skilled in the art) an effective amount of detector molecule, and then surgery occurs after an appropriate time period to have the detector molecule preferentially localize in the lymphoid tissues containing shed tumor antigen, and to establish background levels. Inserted through a cannula at a portal established in a quadrant of the abdominal wall is a laparoscopic probe. The laparoscopic probe is then maneuvered along, and in adjacency with, the colon in scanning the peritoneal cavity for lymphoid tissues containing shed tumor antigen, as indicated by the detection of signal (measurably greater than background signal) emitted by the detector molecule. The lymphoid tissues detected as containing shed tumor antigen may then be surgically removed by laparoscopic surgery. In the case where such lymphoid tissue is difficult to remove, an open laparotomy may be performed, and the areas rescanned to detect and remove lymphoid tissues containing shed tumor antigen.

Another embodiment is the detection of magnetic signals from a detector molecule comprising an affinity molecule, wherein affinity molecule has binding specificity for shed tumor antigen, and wherein the affinity molecule is bound to a magnetic particle. Magnetic particles that may be useful in the immune corrective surgical method according to the present invention may include ferromagnetic, ferrimagnetic, diamagnetic, and paramagnetic particles. Such particles may take the form of beads, crystals, microspheres, and the like. As appreciated by those skilled in the art, the size and composition of the magnetic particles may vary. It is generally known that magnetic particles in the range of 0.3 micron to 1 micron or greater, are rapidly cleared from the blood by the reticuloendothelial system primarily in the liver and spleen, thereby minimizing delivery to other tissues (e.g., lymphoid tissues). Accordingly, magnetic particles for use in vivo with the method according to the present invention include those less than 1 micron in diameter, and preferably 10 nanometers to 30 nanometers in diameter. Other properties of the magnetic particles desirable for in vivo use with the method of the present invention include that they be pharmacologically acceptable; either metabolizable or are metabolically inert; magnetically mapable; and able to concentrate in shed tumor antigen containing lymphoid tissues. To be pharmacologically acceptable, the magnetic particles need to be of an electrostatic nature so as to prevent intravascular clumping; and be biocompatible. Methods of making magnetic particles biocompatible are known to those skilled in the art. For example, magnetic particles may be coated with synthetic polymers (e.g., poly-L-lysine, poly-L-glutamic acid), protein or glycoprotein polymers (e.g., albumin, hemoglobin, gelatin), and polysaccharides (endogenous carbohydrates including starch, glycogen, and dextran) (collectively referred to as "polymers"; see, e.g., U.S. Pat. Nos. 4,247,406 and 5,670,135 for particle types, and coatings). In a related embodiment, the magnetic particles may be coated with both polymers and peptide. In a preferred embodiment, the magnetic particles are coated (noncovalently or covalently using methods known in the art) with a peptide having binding affinity and specificity for shed tumor antigen (e.g., SEQ ID NO:1) in forming detector molecule in a manner that maximizes the presentation of the antigen binding domain(s) of the peptide to optimize interaction with its ligand, shed tumor antigen. Coatings may be used to either optimize this type of binding of affinity molecule to the magnetic particles, and/or may be used to coat the magnetic particles on surfaces of the magnetic particles to which affinity molecule did not bind. Such coatings should be considered in the final size of the detector molecule which utilizes magnetic particles.

An effective amount of such detector molecule may be administered parenterally to the individual; e.g., intravascularly, and preferably into a blood vessel within a short distance of the anatomic site to be scanned. Alternatively, an effective amount of detector molecules are delivered to the lymph nodes and other lymphoid tissue by drainage of interstitially localized preparations through lymph vessels. The objectives of introducing the detector molecule include to maximize the amount of the detector molecule to shed tumor antigen containing-lymphoid tissues of the individual, thereby concentrating the magnetic signal to be detected from detector molecule binding to shed tumor antigen; and that detector molecule not specifically bound, be substantially cleared (blood circulation reduction) from the individual to achieve a background level of signal.

It will be appreciated by those skilled in the art, that an effective amount of the detector molecule administered, and the clearance from the blood circulation, may depend on such factors which include, but are not limited to, one or more of the character of the magnetic particle (incuding a coating if a coating is used) as to chemical and/or physical characteristics (e.g., ionic properties, size, shape, reactive groups), and interactions with other macromolecules and/or cells in the circulation. A sensitive magnetometer probe, capable of detecting the magnetic signal emitted by the effective amount of detector molecule bound to shed tumor antigen localized and concentrated in the lymphoid tissue scanned, may be used for one or more of (a) determining the distribution of detector molecules in shed tumor antigen-containing lymphoid tissue; (b) determining the time period for maximal detector molecule (comprising a coated magnetic particle) concentration in shed tumor antigen containing-lymphoid tissue; (c) detecting the achievement of a background level of signal; and (d) determining detector molecule (with magnetic particle) localization and concentration by differential comparisons of mappings taken over a time interval. The dosage of the detector molecule to be administered will vary depending on such factors including, but not limited to, those factors that relate to clearance from the blood circulation, the efficiency of binding the affinity molecule to magnetic particles, the availability of the shed tumor antigen binding domain(s) of the affinity molecule when bound to the magnetic particle, the strength of magnetic signal emitted from the magnetic particles, and the sensitivity of the magnetometer probe to detect the concentrated magnetic signal in shed tumor antigen-containing lymphoid tissue. One skilled in the art would be able to determine an effective amount of detectable molecule to be administered, and the time period necessary to achieve a background level of signal before immune corrective surgery is performed. For purposes of illustration, but not limitation, an effective amount of affinity molecule, used to form an effective amount of the detector molecule, may be determined by a medical practitioner to be in a range of from about 1 μg/kg body weight to 1 mg/kg body weight or more. The amount of magnetic particles used to form an effective amount of detector molecule may also be determined by a medical practitioner. For example, intravenous injections of magnetic particles that have been used previously in the art include 1 to 10 mg of particles per kg of body weight of the patient, and up to 20 to 45 mg per kg of body weight (see, e.g., U.S. Pat. No. 4,735,796). Magnetometer probes which have been described as detecting magnetic particles in vivo are known in the art (see, e.g., U.S. Pat. Nos. 5,494,035; 5,444,372; and 5,384,109), and may be used in the method according to the present invention. According to this embodiment, detector molecule comprising magnetic particles may be used to detect shed tumor antigen containing lymphoid tissues, thereby enabling a surgeon to surgically remove all or that portion of that detected lymphoid tissue from the individual.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. A method for immune corrective surgery comprising the steps of:

administering parenterally to an individual an effective amount of detector molecule, wherein the detector molecule comprises an affinity molecule bound to a detectable label, wherein the affinity molecule is selected from the group consisting of a monoclonal antibody, a peptide, a lectin, and an aptamer, and wherein the detectable label is selected from the group consisting a radioisotope, and a magnetic molecule;

subjecting the individual to a time interval sufficient for allowing the detector molecule to localize and concentrate in lymphoid tissue containing shed tumor antigen, if present, and to achieve a background level of signal;

subjecting the individual to a surgical procedure wherein an instrument or probe, capable of distinguishing and localizing signal emitted from localized detector molecule bound to shed tumor antigen, is used to scan lymphoid tissues for localization of the detector molecule, and wherein if shed tumor antigen is detectably present in a lymphoid tissue, a signal of measurably greater intensity or strength than that of the background level is detected by the instrument or probe; and surgically removing from the individual all, or that portion, of the lymphoid tissue detected as containing shed tumor antigen.

2. The method of claim 1, wherein the detector molecule has binding specificity for an epitope on the shed tumor antigen, wherein the epitope is selected from the group consisting of sTn antigen, Tn antigen, a sialic acid containing epitope on a carbohydrate chain, and a combination thereof.

3. The method of claim 2, wherein the shed tumor antigen is mucin.

4. The method of claim 1, wherein the detector molecule is a peptide for use as a detector molecule, wherein the peptide comprises an amino acid sequence of SEQ ID NO:1.

5. The method of claim 1, further comprising rescanning for residual signal in areas surrounding the surgically removed lymphoid tissue detected as containing shed tumor antigen.

6. The method of claim 5, further comprising surgically removing lymphoid tissue detected as containing shed tumor and detected as a source of the residual signal.

7. The method of claim 1, wherein the individual is an individual selected from the group consisting of an individual having a primary tumor comprising a solid, non-lymphoid tumor, an individual having metastases of a solid, non-lymphoid tumor, an individual with a pre-cancerous condition comprising transformed cells of ductal epithelial origin which release shed tumor antigen, an individual who is at high risk for developing a solid, non-lymphoid tumor, and an individual who has been treated for a solid, nonlymphoid tumor and who carries a risk of recurrence.

8. The method of claim 1, wherein the effective amount of the detector molecule is administered intravenously.

* * * * *

SEQUENCE LISTING

```
<160> NUMBER OF SEQ ID NOS: 1

<210> SEQ ID NO 1
<211> LENGTH: 244
<212> TYPE: PRT
<213> ORGANISM: Mus sp.

<400> SEQUENCE: 1

Ala Met Gly Gln Val Gln Leu Gln Gln Ser Asp Ala Glu Leu Val Lys
1               5                   10                  15

Pro Gly Ala Ser Val Lys Ile Ser Cys Lys Ala Ser Gly Tyr Thr Phe
            20                  25                  30

Thr Asp His Ala Ile His Trp Val Lys Gln Lys Pro Glu Gln Gly Leu
        35                  40                  45

Glu Trp Ile Gly Tyr Phe Ser Pro Gly Asn Gly Asp Ile Lys Tyr Asn
    50                  55                  60

Glu Lys Phe Lys Gly Lys Ala Thr Leu Thr Ala Asp Lys Ser Ser Ser
65                  70                  75                  80

Thr Ala Tyr Met Gln Leu Asn Ser Leu Thr Ser Glu Asp Ser Ala Val
                85                  90                  95

Tyr Phe Cys Lys Arg Ser Tyr Gly Asn Tyr Asp Tyr Trp Gly Gln Gly
            100                 105                 110

Thr Thr Leu Thr Val Ser Ser Gly Gly Gly Gly Ser Gly Gly Gly Gly
```

-continued

```
        115                 120                 125

Ser Gly Gly Gly Gly Ser Asp Ile Leu Leu Thr Gln Ser Pro Ala Ile
    130                 135                 140

Leu Ser Val Ser Pro Gly Glu Arg Val Ser Phe Ser Cys Arg Ala Ser
145                 150                 155                 160

Gln Asn Ile Gly Thr Ser Ile His Trp Tyr Gln Gln Arg Thr Asn Gly
                165                 170                 175

Ser Pro Arg Leu Leu Ile Lys Tyr Ala Ser Glu Ser Val Ser Gly Ile
            180                 185                 190

Pro Ser Arg Phe Ser Gly Ser Gly Ser Gly Thr Asp Phe Thr Leu Ser
        195                 200                 205

Ile Asn Ser Val Glu Ser Glu Asp Ile Ala Asp Tyr Tyr Cys Gln His
    210                 215                 220

Thr Asn Ser Trp Pro Thr Thr Phe Gly Gly Gly Thr Lys Leu Glu Ile
225                 230                 235                 240

Lys Leu Glu His
```